United States Patent [19]

Schaüfele

[11] 4,062,240
[45] Dec. 13, 1977

[54] DOSING DEVICE FOR A LIQUID CHROMATOGRAPH

[75] Inventor: Günter Richard Schaüfele, Karlsruhe, Germany

[73] Assignee: Hewlett-Packard GmbH, Boblingen, Germany

[21] Appl. No.: 752,710

[22] Filed: Dec. 20, 1976

[30] Foreign Application Priority Data

Jan. 9, 1976 Germany .............................. 2600622

[51] Int. Cl.² ............................................. G01N 1/00
[52] U.S. Cl. ................................................. 73/422 GC
[58] Field of Search ................................... 73/422 GC

[56] References Cited

U.S. PATENT DOCUMENTS

| | | | |
|---|---|---|---|
| 3,362,228 | 1/1968 | Stuben | 73/422 GC |
| 3,681,996 | 8/1972 | Crist | 73/422 GC X |
| 3,827,303 | 8/1974 | Shiina | 73/422 GC |

Primary Examiner—Charles A. Ruehl
Assistant Examiner—Joseph W. Roskos
Attorney, Agent, or Firm—Stephen P. Fox

[57] ABSTRACT

A dosing device for a liquid chromatograph includes an axially movable shank. The shank is guided in packing sleeves and has a notch or cavity for receiving a sample and transferring it between a sample chamber and a high pressure chamber by axially moving the shank. The high pressure chamber is coupled to the chromatograph flow system between the pump and the column. A shutter is provided for closing the notch. In the closed position, the shutter and the shank together form a smooth common surface.

5 Claims, 1 Drawing Figure

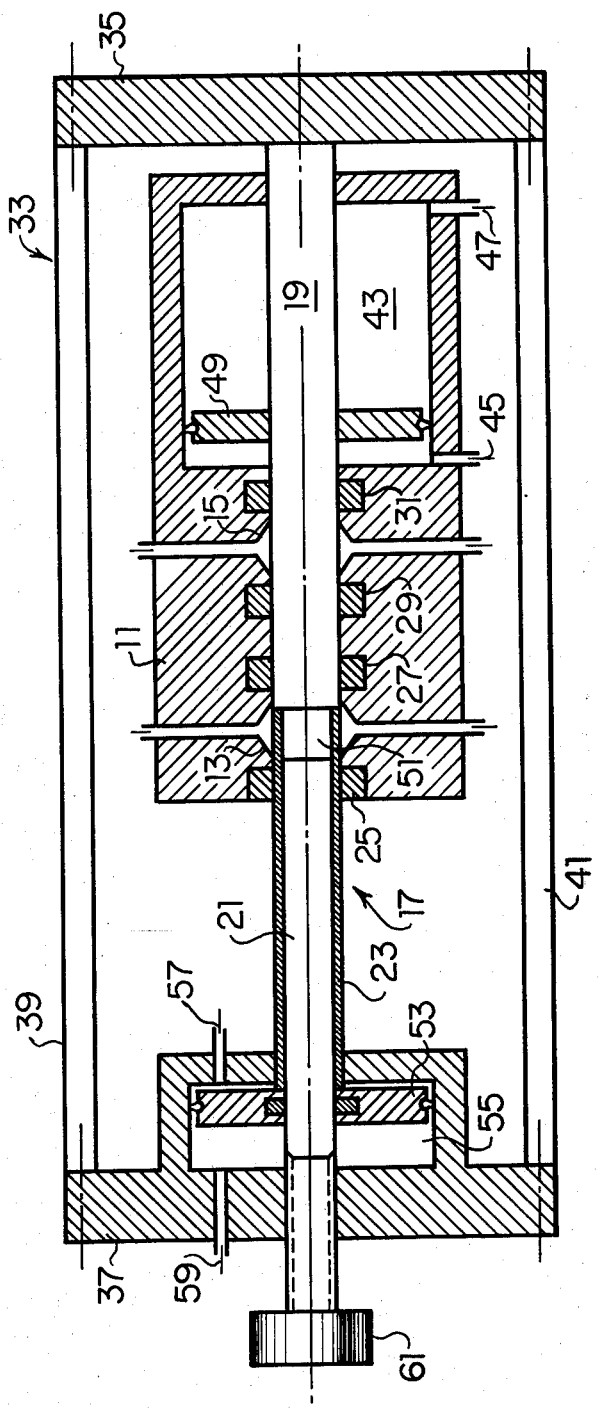

DOSING DEVICE FOR A LIQUID CHROMATOGRAPH

BACKGROUND OF THE INVENTION

Dosing devices for liquid chromatographs are known which comprise an actually movable shank being guided in packing sleeves and having a notch capable of receiving a sample and transferring it between a sample chamber and a high pressure chamber through at least one packing sleeve. The high pressure chamber is typically connected to the chromatograph flow system between the pump and the column. Such dosing devices have the disadvantage that the notch must be moved through the packing sleeve which forms a seal between the two chambers. Since this seal must withstand high pressures, the packing sleeve must be strongly pressed against the shank. This causes a certain deformation of the packing sleeve. Thus, it penetrates into the notch when the notch is passing the packing sleeve, even if the notch has rounded edges. The resulting substantial friction effect leads to abrasion of the packing sleeve particles. Consequently, the sample becomes contaminated, and the seal is demolished after a relatively short operation time.

SUMMARY OF THE INVENTION

The present invention provides an improved dosing device which avoids abrasion of the sealing material of the packing sleeve. According to the illustrated embodiment of the invention, a dosing device for a liquid chromatograph includes an axially movable shank which is guided in packing sleeves. The shank has a notch or cavity capable of receiving a sample and transferring the sample by axially moving the shank through at least one packing sleeve between a sample chamber and a high pressure chamber. The high pressure chamber is coupled to the chromatograph flow system between the pump and the column.

A movable shutter closes the notch and forms together with the shank a smooth common surface in the closed position. Preferrably the shutter is a tube which surrounds the shank and is axially movable thereon.

BRIEF DESCRIPTION OF THE DRAWINGS

The single FIGURE is a longitudinal cross-section view of the preferred embodiment of the invention.

DESCRIPTION OF THE PREFERRED EMBODIMENT

Referring to the drawing there is provided a chamber housing 11, including a sample chamber 13 and a high pressure chamber 15. Both chambers have pipe connections for coupling sample chamber 13 to a sample reservoir and for coupling high pressure chamber 15 between a pump and a column of a liquid chromatograph. A shank assembly 17 passes through both chambers 13, 15. Shank assembly 17 includes a first shank portion 19, a second shank portion 21 and a tube 23. Chambers 13 and 15 are isolated from each other and sealed against the environment by packing sleeves 25, 27, 29 and 31.

Shank portions 19 and 21 are interconnected by a frame 33. Frame 33 comprises two traverse plates 35 and 37 connected respectively to the shank portions 19, 21. Plates 35, 37 are supported in spaced-apart relation by interconnecting bars 39 and 41.

A hydraulic cylinder 43 forms an integral part of chamber housing 11, and has fluid pipe connections 45 and 47. A piston 49 is moved within cylinder 43 by applying fluid under pressure through pipes 45, 47. Piston 49 is fastened to shank portion 19. By moving piston 49, a notch 51 is formed between shank portions 19, 21 is transferrable from chamber 13 into chamber 15 and vice versa, as hereinafter described.

Shank portion 21 has a smaler diameter than shank portion 19 and is surrounded by tube 23 having the same outer diameter as shank portion 19. Tube 23 is fastened to a piston 53 which is movable within a cylinder 55 connected to traverse plate 37. By supplying fluid under pressure to pipe connections 57 and 59, piston 53 and the attached tube 23 are movable in such a manner that tube 23 either closes notch 51 or leaves it open.

The volume of notch 51 may be modified by means of an adjusting screw 61 connected to shank portion 21.

The operation of the illustrated embodiment is as follows: Assume the starting position is as illustrated in the figure. By supplying fluid under pressure to pipe connection 57, tube 23 is moved left so that notch 51 is opened. A sample liquid supplied to chamber 13 then fills notch 51. Next tube 23 is moved right by supplying fluid under pressure to pipe connection 59. Thus, notch 51 is closed and a predetermined amount of sample liquid is enclosed in notch 51. Thereafter, fluid under pressure is supplied to pipe connection 45 resulting in a movement to the right of piston 49 together with the entire shank assembly 17 and frame 33. Notch 51 is thereby shifted from chamber 13 to chamber 15. In chamber 15, notch 51 is opened by left movement of tube 23, and the enclosed sample liquid is supplied to chamber 15, i.e., the high pressure section of the liquid chromatograph. After closing of notch 51 by means of tube 23, shank assembly 17 may be again moved to the left, and a subsequent sample may be injected in the above-described manner.

Shank assembly 17 is moved only when tube 23 is in the closing position as illustrated in the figure. Since tube 23 and shank portion 19 have the same outer diameter and are commonly ground, there is no edge on the shank assembly 17 which could destroy packing sleeves 27 and 29, when notch 51 passes them. In the closing position, there is merely a remaining ring notch which by grinding of the shank and tube surfaces may be made so fine that an overall smooth surface is created.

We claim:

1. Dosing apparatus for a liquid chromatograph comprising:
   means defining a first sample receiving chamber and an adjacent second chamber connectable between the pump and column of a chromatograph flow system; and
   sample transferring means disposed in communication with said first and second chambers, said transferring means including:
   shank means formed to define a sample cavity therein, said shank means being axially movable between said first and second chambers to position said cavity in a selected one of said chambers; and
   movable shutter means disposed on said shank for closing said cavity.

2. The apparatus of claim 1, further including packing means disposed in said means defining said chambers for guiding said shank and isolating said chambers from each other and the environment.

3. The apparatus of claim 2, wherein said shutter means surrounds and is axially movable on said shank means, said shutter means forming together with said shank means a smooth common surface when said shutter means closes said cavity.

4. The apparatus of claim 3, wherein said movable shutter means includes a tube coaxially disposed on said shank means.

5. The apparatus of claim 1, wherein said shank means comprises two axially movable portions forming said cavity therebetween; and further including bridge means for connecting said two movable portions, said bridge means being longitudinally adjustable to thereby adjust the volume of said cavity.

* * * * *